United States Patent [19]

Allton

[11] Patent Number: 5,207,641
[45] Date of Patent: May 4, 1993

[54] MEDICAL ROTARY VALVE HAVING ASPIRATION, INSUFFLATION AND AN INTERMEDIATE FLUSHING POSITIONS

[75] Inventor: Robert A. Allton, Mississauga, Canada

[73] Assignee: Bird Medical International Inc., Mississauga, Canada

[21] Appl. No.: 717,053

[22] Filed: Jun. 18, 1991

Related U.S. Application Data

[63] Continuation-in-part of Ser. No. 351,594, May 15, 1989, abandoned.

[51] Int. Cl.$^5$ ............................................. A61M 1/00
[52] U.S. Cl. .................................. 604/32; 137/625.22
[58] Field of Search ...................... 604/248, 32, 35, 27, 604/246; 137/625.41, 625.46, 625.47, 625.22

[56] References Cited

U.S. PATENT DOCUMENTS

| | | | |
|---|---|---|---|
| 3,057,370 | 10/1962 | Hamilton | 137/625.47 |
| 3,078,848 | 2/1963 | Milbert | 604/32 |
| 3,253,617 | 5/1966 | Beckett | 137/625.69 |
| 3,276,472 | 10/1966 | Jinkens et al. | 604/248 |
| 3,586,049 | 6/1971 | Adamson | 137/625.41 |
| 3,750,704 | 8/1973 | Burke et al. | 137/625.47 |
| 3,834,372 | 9/1974 | Turney | 604/248 |
| 4,193,406 | 3/1980 | Jinotti | 128/204.18 |
| 4,207,923 | 6/1980 | Guirtino | 137/625.47 |
| 4,219,021 | 8/1980 | Fink | 604/248 |
| 4,593,717 | 6/1986 | Levasseur | 137/625.47 |
| 4,595,005 | 6/1986 | Jinotti | 604/248 |
| 4,705,073 | 11/1987 | Beck | 137/625.69 |
| 4,950,230 | 8/1990 | Kendell | 604/32 |

Primary Examiner—C. Fred Rosenbaum
Assistant Examiner—Mark W. Bockelman
Attorney, Agent, or Firm—Donald E. Hewson

[57] ABSTRACT

A dual purpose catheter valve especially for oxygen insufflation and mucous suction from the lungs and trachea system of a patient, is provided. The body has two snap-fitted generally cylindrical parts, mounted for relative rotation, with an oxygen port, suction port and catheter port on the outer body part for connection to the respective valves, and ports formed in the wall of the inner body part. There are two pairs of inner body ports, one pair for alignment with the oxygen port and the catheter port of the outer body part, the other pair for alignment with the suction port and the catheter port of the outer body part. When one of the oxygen or suction ports is aligned for fluid communication to the interior of the body and to the catheter port, the other of the oxygen or suction ports is shut off by a wall portion of the inner body part. There is a neutral position of the two body parts when rotated relative to each other, where neither the oxygen nor suction ports communicates to the catheter, so that there may be a settling of the system when switched from insufflation to aspiration, or vice versa, and so that the change from one to the other is not abrupt, thereby reducing the risk of trauma to the patient. The oxygen and suction ports do communicate with each other in this neutral position.

9 Claims, 3 Drawing Sheets

MEDICAL ROTARY VALVE HAVING ASPIRATION, INSUFFLATION AND AN INTERMEDIATE FLUSHING POSITIONS

CROSS-REFERENCE

This application is a Continuation-In-Part Application of Ser. No. 07/351,594 filed May 15, 1989, now abandoned.

FIELD OF THE INVENTION

This invention relates to a suction catheter valve, being an input and extraction catheter valve for use in inputting gas (usually oxygen) to a body cavity and extracting fluid from the body cavity. The invention is especially directed to a catheter valve for insufflation of oxygen into the lungs, and aspiration of fluids from the lungs and trachea system.

BACKGROUND OF THE INVENTION

Catheter devices to draw fluids from various parts of the body are known, including catheter valves for aspirating the lungs. Such catheter valves for aspirating the lungs (and trachea) may be provided with means for insufflating the lungs with oxygen at least prior to aspiration so as to prevent or minimize hypoxia and related syndromes in the patient. At least one commonly used device comprises a catheter tube connectable to a source of suction and provided with a suction relief orifice openable and closable by finger pressure of an operator. By using his finger—usually the thumb—as a plug in the orifice, the operator may open and close, or partially open, the orifice to control the rate of suction. Use of this type of device necessitates prior insufflation of oxygen with the attendant risks of preliminary overdosage of oxygen, and there is no means of providing extra oxygen during this suction procedure. Moreover, even a skilled operator is needed for the aspiration or suction procedure, since the opening and closing of the suction relief orifice may tend to make the aspiration very jerky. This prior art device is generally considered to as a "thumb control valve", and is used only for suction or aspiration procedures.

PRIOR ART

Devices designed for both supply of oxygen and for aspiration have tended to follow the general design of spool valves, which are adapted to connect alternate ones of the plurality of conduits with another conduit. Often such spool valves have comprised a plunger spring biased into one position in a valve body, in which a first bore in the plunger connects one conduit of a plurality of conduits with another conduit. An operator may depress the plunger against the spring bias to another position such that the first bore moves out of register with the one conduit, and a second bore moves into register with a different conduit of the plurality of conduits to connect the second bore with the other conduit. Such a spool valve is described in U.S. Pat. No. 3,253,617 issued May 31, 1966 to BECKETT. The bores in such valves were traditionally made by drilling.

Other catheter valves of the gate or slide valve type are disclosed in U.S. Pat. No. 4,193,406 issued Mar. 18, 1980 to JINOTTI, and in U.S. Pat. No. 4,705,073 issued Nov. 10, 1987 to BECK.

For catheterization, these patented valves represented a considerable advance over the simple valve which required heavy pre-oxygenation. These valves enabled aspiration to be alternated with oxygen insufflation, as required. For oxygen insufflation and fluid withdrawal from the lungs it is important that the device be sufficiently inexpensive that it may be discarded after a single use. Some patients may have fluid drawn from their lungs as often as six times a day, possibly over long periods of time. The patented devices are widely used in treating newborns, especially premature infants who are subject to respiratory problems and may need frequent aspirations. As a result of the extremely large number of aspirations necessary on various patients in any period, it is important that the price of these disposable devices be as low as possible since vast numbers will be used.

However, the prior art valves required a relatively large number of parts including the valve body, the plunger, the spring providing spring bias to the plunger and sealing means to ensure that potentially infective mucous does not contaminate the atmosphere and particularly the attending physician, nurse, or other healthcare personal; or that potentially infective mucous does not contaminate any part of the device not along its flow path. Thus, sealing means must be provided on the plunger to seal the channels from communication with a chamber containing the spring, and from the atmosphere.

It would be desirable to simplify such devices to reduce the number of parts and to reduce the costs. Moreover, the prior art devices have a practical disadvantage. When fluid such as mucous is being aspirated and the need to insufflate oxygen becomes apparent, the operator may merely depress the plunger to change from the aspiration mode to insufflation. Other than with the dual lumen catheter version of the Jinotti valve, however, the change is abrupt, and any fluid in the catheter tube may be blown back into the lungs. Such forced blow-back may cause lung damage, and it would be especially advantageous to avoid such blow-back in the case of infants whose lungs are at least fragile and may not be fully developed. A neutral position for stabilization when changing from aspiration to insufflation assists in reducing the risk of blow-back, but not all prior art devices have such an arrangement, and those that do are generally quite expensive.

SUMMARY OF THE INVENTION

The present invention provides a catheter valve that connects an oxygen port and a suction port to a catheter port and allows for alternate insufflation and aspiration, having a neutral position in which neither aspiration nor insufflation takes place at the catheter port of the device. This allows for a neutral transition between aspiration and insufflation so that the change from one to the other is not abrupt, thereby reducing the risk of trauma to the patient. Further, in this neutral position, the oxygen port and the suction port are in fluid communication so that any mucous contained within the valve is generally cleared by the oxygen passing from the oxygen port to the suction port.

Moreover, it is possible to make the device of the present invention with fewer parts than has previously been possible, and the parts may be very simple mouldings. The cost of the inventive device may, therefore, be minimized.

According to the present invention there is provided an input and extraction catheter valve for the respective input of fluid (specifically gases) or extraction of fluid with respect to a body cavity comprising: a valve housing including a first housing piece having an outer cylindrical wall through which, in spaced relationship therearound, there are at least a fluid input port, an extraction port and a catheter port. A second housing piece is provided, having an inner cylindrical wall in fluid tight relationship and concentric with the outer cylindrical wall of the first housing piece, the first and second housing pieces being rotatable with respect to each other about the axis of the inner and outer cylindrical walls. The inner cylindrical wall has a first pair of ports therethrough, and a first shut-off portion of the wall, whereby the catheter port and fluid input ports are in fluid communication with the interior of the housing and the extraction port is covered and shut off, when there is a first relative position between the inner and outer housing pieces. The inner cylindrical wall also has a second pair of ports therethrough, and a second shut-off portion of the wall, whereby the catheter port and the extraction port are in fluid communication with the interior of the housing and the fluid intake port is covered and shut off, when there is a second relative position of the housing pieces. The inner cylindrical wall also has a third shut-off portion to shut off the catheter port when there is a third relative position of the housing pieces, which third relative position is intermediate the first and second relative positions.

Manually operable means are provided to rotate the housing parts relative to one another between the first, second and third positions with such rotation being substantially less than 90°, typically about 50°, and is moved only a short distance—commonly known as a "throw" distance—to obtain this movement of less than 90°. Such means is preferably thumb operable lever which would therefore require a relatively short "throw" distance between all three positions, with a typical throw distance being about 0.5".

BRIEF DESCRIPTION OF THE DRAWINGS

Several exemplary embodiments of the invention will now be described with reference to the accompanying drawings, in which.

DESCRIPTION OF THE PREFERRED EMBODIMENTS

Figure 1:
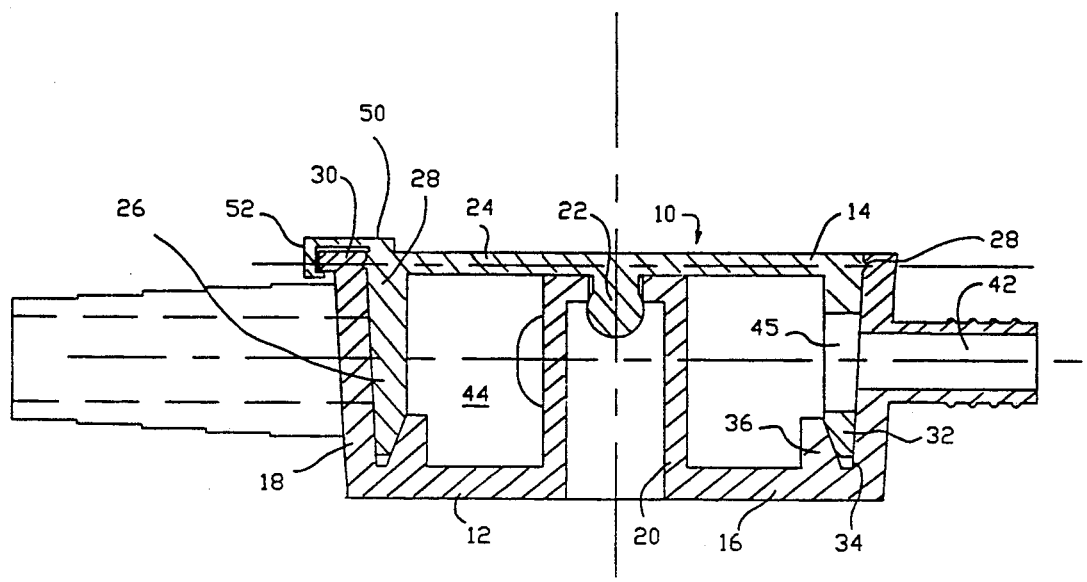
FIG. 1 is a vertical section through a first embodiment of a dual purpose catheter valve, according to the present invention.

The following discussion is in respect of two specific embodiments, each of which is exemplary of the dual purpose catheter valve of the present invention. For the most part, similar reference numerals are used for the identical parts and features of both embodiments being discussed. The operation of the dual purpose catheter valve of the present invention will be discussed particularly with reference to the embodiment shown in FIGS. 3 to 6; and the basic structure of the dual purpose catheter valve of the present invention will be discussed in greater detail with respect to the first embodiment shown in FIGS. 1 and 2.

Figure 2:
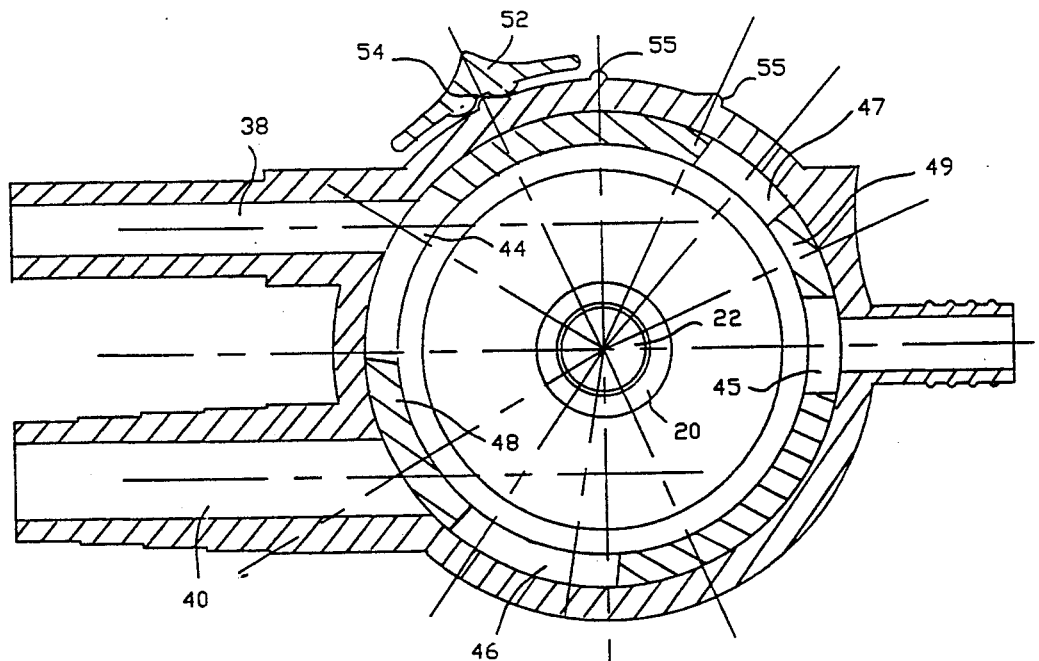
FIG. 2 is a horizontal section through the dual purpose catheter valve of FIG. 1.

The drawings show a catheter valve 10 comprising an outer housing piece 12 and an inner housing piece 14. The outer housing piece has a generally circular base 16 and an upstanding cylindrical wall 18. As seen in FIGS. 1 and 2, the outer housing piece also includes an upstanding central hollow post 20 acting to locate a boss 22 of the inner housing piece 14. The post 20 and boss 22 are, however, not strictly necessary; and are not included in the second embodiment of the present invention as shown in FIGS. 3 to 6.

The inner housing piece 14 comprises a generally circular top 24 having a depending cylindrical wall 26. The dimensions of walls 18 and 26 are such that they fit together in close fitting relationship but with sufficient clearance between them that the housing pieces 12 and 14 are rotatable with respect to each other. Sealing means for fluid tight sealing are provided between the inner and outer cylindrical walls 18 and 26.

The sealing means may conveniently be, when the housing pieces are made of suitable material such as polyethylene or polypropylene, at least one continuous bead 28 on one of the inner or outer walls 26 and 18 engaging a complementary groove 30 on the other of the inner and outer walls 26 and 18. The dimensions of bead 28 and groove 30 may be such that they may be engaged by snap fitting on assembly of the housing pieces 12 and 14. Annular sealing rings or O-rings could, however, be used.

Additional sealing means may be provided by wedge fitting a lower tapered portion 32 of the inner wall 26 into a circular groove 34 formed at the base of the housing piece 12, by an upstanding circular wedge shaped ridge 36. In the embodiment shown in FIGS. 3 to 6, the tapering of either or both the lower portion 32 of inner wall 26 and the wedge-shaped ridge 36 may be non-linear, whereas in the embodiment of FIGS. 1 and 2 it is shown as linear. The non-linear embodiment, which is essentially a radiused outer face on the ridge 36, may add to the ease of relative rotation between the housing pieces 12 and 14 by reducing the static friction between them.

The outer housing piece 12 is provided with three ports, an oxygen insufflation port 38, a suction or aspiration port 40, and a catheter port 42, spaced around its periphery. Each port 38, 40 and 42 is provided with suitable connection means for an oxygen supply tube, a suction tube, and a catheter tube, respectively. As shown in both illustrated embodiments, the three ports are in parallel relationship one with another, but this has no special significance. It does allow the catheter valve to be held comfortably and easily in one hand, which is important for proper use.

It is quite important, however, that the oxygen port 38 and the suction port 40 (and the associated ports 44 and 46) be spaced apart by a reasonably short distance around the periphery of the outer housing piece 12 and inner housing piece 14 respectively. This short distance allows for a short "throw" distance between the insufflation and oxygenation positions. A distance of about 0.5" has been found to be preferable and easily usable. This corresponds to an angular rotation of about 50° for the size of the catheter valve of the present invention.

The short throw distance means that the inner housing piece can be moved rotatably with respect to the outer housing piece between these two positions by movement of the manually operable means, with the manually operable means being a thumb operated lever that is operated simply by flexing the thumb on the hand that is holding and using the catheter valve.

Moreover, by placing these ports close together if a number of operations greater than two is required, such as by insufflation or another gas as well as oxygen, then additional ports may be provided. It is believed that this cannot be achieved by prior art valves that have three ports spaced 90° apart from one another.

The cylindrical wall 26 of the inner housing piece 14 is provided with a first pair of ports 44 and 45, and a second pair of ports 46 and 47 for alternate registration with the oxygen insufflation port 38 and the catheter port 42, and with the aspiration port 40 and the catheter port 42, in respective first and second positions of the housing pieces 12 and 14, relative to each other.

Figure 4:
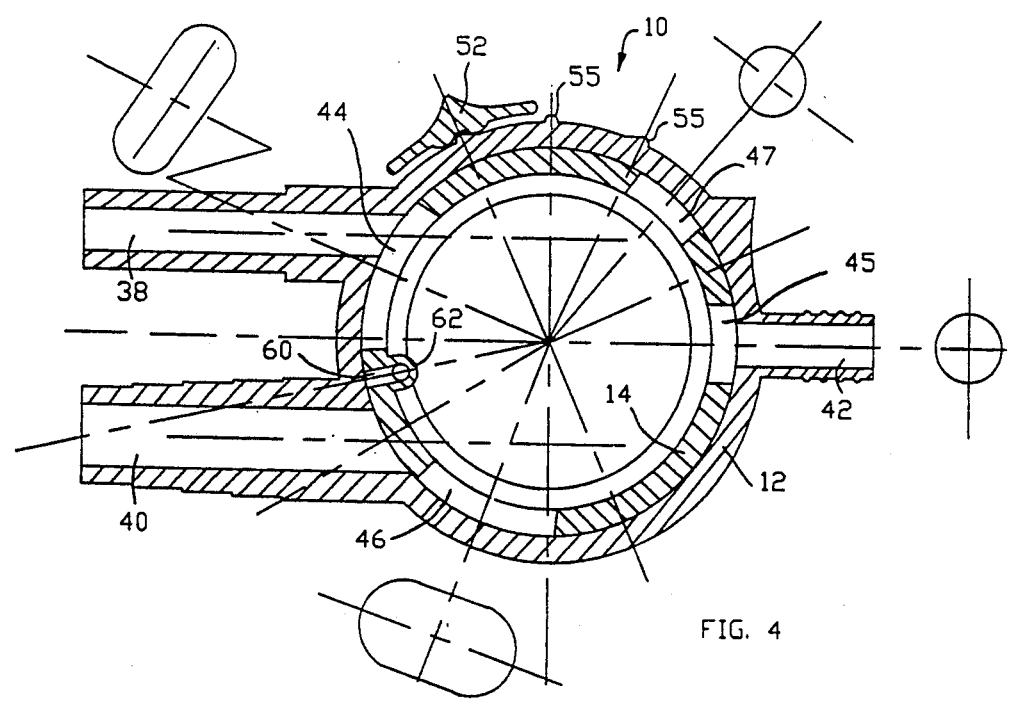
FIG. 4 is a horizontal section through the dual purpose catheter valve of FIG. 3, with the housing pieces in a first position similar to what is shown in FIG. 2, and with an indication of the shape of the port openings through the walls of the inner housing piece.

As may be seen in each of FIGS. 2 and 4, in a first position of housing pieces 12 and 14, the first pair of ports 44 and 45 communicate the oxygen line with the catheter tube, respectively, the port 44 registering with oxygen insufflation port 38, and port 45 registering with catheter port 42. In this position, a shut-off region 48 of inner wall 26 closes the aspiration port 40.

Figure 5:
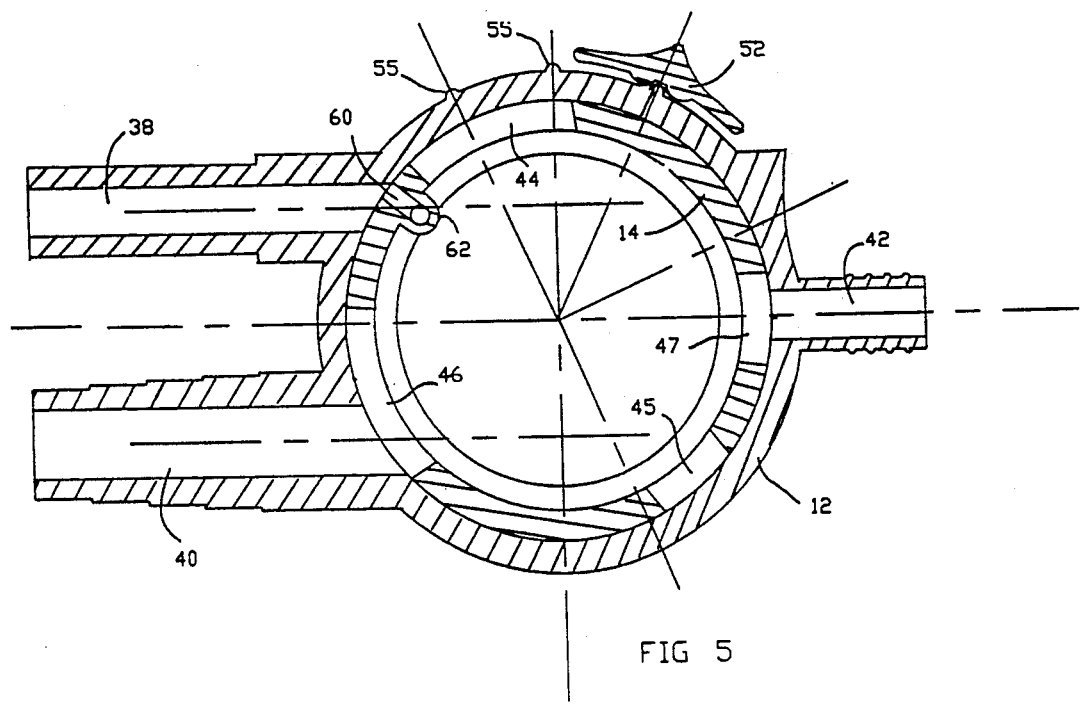
FIG. 5 is a horizontal view similar to FIG. 4, showing the housing pieces in a second position.

As shown in FIG. 5, in a second position of the housing pieces 12 and 14, the second pair of ports 46 and 47 provide communication between the aspiration tube and the catheter tube, respectively, the port 46 registering with the aspiration port 40, and the port 47 registering with the catheter port 42.

A dual purpose catheter valve according to the present invention generally also has a further feature, in that there is a third rotated position of the housing pieces 12 and 14 relative to each other, enabling a neutral operative condition in which neither the suction line nor the oxygen supply line is connected to the catheter tube. Such a neutral position allows natural settling or possibly even flow back of any mucous or other fluid trapped in the catheter tube when changeover is made, and it avoids the risks inherent in switching abruptly from aspiration to insufflation with forced blow-back of mucous.

Figure 6:
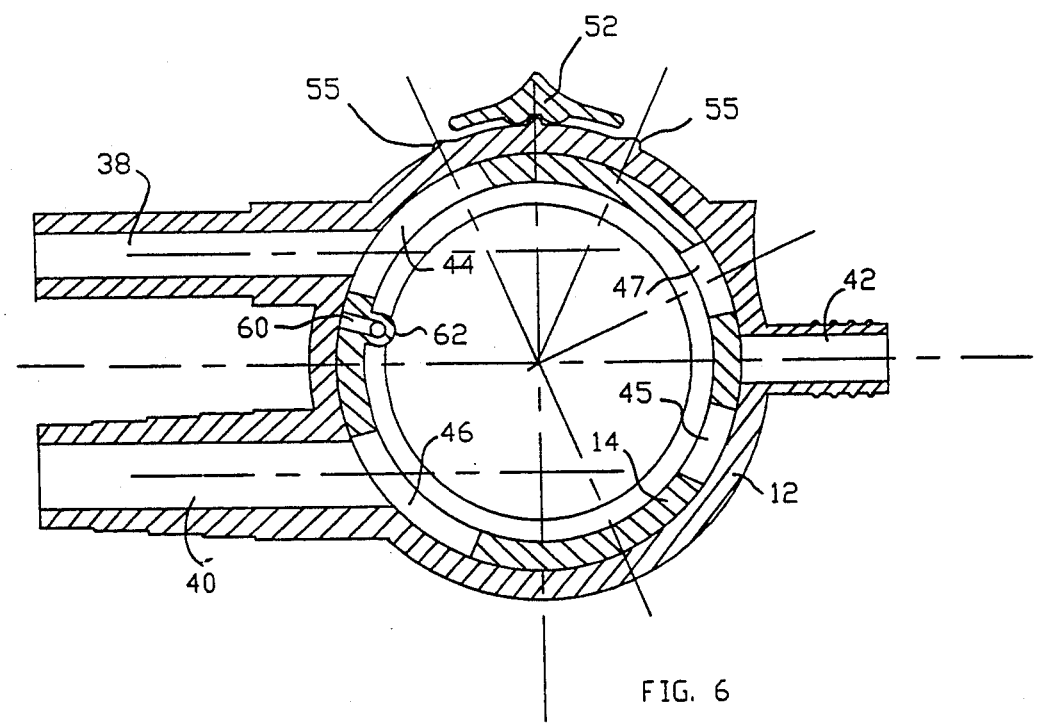
FIG. 6 is a horizontal section similar to FIGS. 4 and 5, and showing the housing pieces in a third position which is intermediate the first and second positions.

The third or intermediate position of the housing pieces 12 and 14 is shown in FIG. 6. Here, the shut-off region 48 closes neither the insufflation port 38 nor the aspiration port 40, but is positioned therebetween. The oxygen port 38 and the suction port 40 are in fluid communication with each other. The flow of oxygen passes from the oxygen port 38 and into the catheter valve 10 where it clears mucous from the interior of the catheter valve 10. The oxygen and mucous are removed from the catheter valve 10 through the suction port 40. In this manner, mucous is cleared from the catheter valve 10 after aspiration and before subsequent insufflation. Thus, mucous contained in the catheter valve 10 is not blown back into the lungs. The shut-off region 49 closes the catheter port 42 such that there is no aspiration or insufflation through the catheter port 42. This provides a transition phase between aspiration and insufflation so that switching from aspiration to insufflation, and vice versa, is less traumatic. It also allows the catheter port 42 to be in a neutral state for any length of time, as desired.

It will be noted that FIG. 4 also includes an indication of the shape of each of ports 44, 45, 46 and 47. Generally, each of the ports 45 and 47—the ports which will align themselves with the catheter port 42—are circular, whereas the ports 44 and 46—which will align themselves with the oxygen line and the suction line, respectively—are oblong in nature. This ensures that connection will be made between the oxygen port 38 and the suction port 40 so as to cause oxygen to flow between the oxygen port 38 and the suction port 40 so as to clear the catheter valve of mucous.

Conveniently, the oxygen port 38 and the suction port 40 should be large enough that a correct flow of oxygen at the standard hospital supply pressure of 50 psi is assured. Moreover, the suction port 40 must be large enough that heavy mucous (or highly viscous fluids) may be aspirated. Moreover, each port should be located, as they are by the present invention, such that there is no interference of any of the tubes or the connectors therefore with one another. Thus, there is an essentially "inline" alignment of the oxygen and suction ports with the catheter tube.

Conveniently, a lever 50 extends upwardly and outwardly from the top 24 of inner housing port 14 for manual turning of the housing piece 14 relative to housing piece 12. It is preferable that each position of the lever 50 and housing pieces 12 and 14 is not only marked, but further indicated by stop means engagable and disengagable by snap fitting. For example, lever 50 may be provided with a downwardly extending portion 52 having a groove 54 resiliently engagable with latching knobs 55 provided on an outer surface of the outer wall 18, one for each of the three positions. Advantageously, stops 56 and 58 are provided to ensure a suitable limitation of rotation of the housing piece 14 relative to the housing piece 12.

Figure 3:
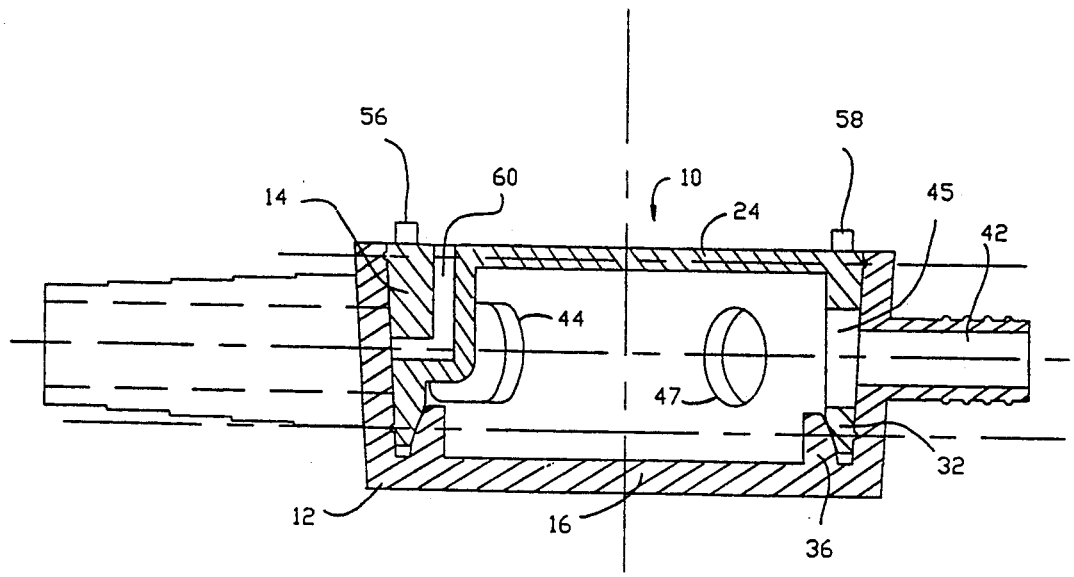
FIG. 3 is a vertical section similar to FIG. 1, through a second embodiment of a dual purpose catheter valve according to the present invention.

The second embodiment of the present invention, shown in each of FIGS. 4 to 6, and in FIG. 3, shows an optional oxygen relief port 60, Which is shown in the illustrations as being formed through the wall of the housing piece 14 and which extends upwardly through the interior of a projection 62 formed on the inner surface of the inner wall 26. The particular purpose for the oxygen relief port, if present, is shown when the housing pieces are in their second position as indicated in FIG. 5. There, the port 46 is aligned with the suction portion 40, so that the interior of the dual purpose catheter valve of the present invention is being evacuated— that is, it is at a lower gauge pressure than the ambient. However, it will be remembered that the oxygen port 38 remains connected to the oxygen supply, and therefore remains pressurized. Thus, the oxygen relief port may serve to preclude the possibility of oxygen leaking into the interior of the device during the suction procedure, and may therefore by optionally provided. The relief port 60 will communicate with an opening (not shown) in the top surface 24 of the inner housing piece 14.

There has been described a dual purpose catheter valve, of which a number of the principle advantages include the fact that it may be easily made of two plastic pieces that are injection moulded, and that to the assembled valve there may then be secured a catheter. There are no additional parts or pieces required, such as annular O-rings or springs.

Because the dual purpose valve of the present invention has three positions, whereby it may be set for oxygen insufflation, suction, or a neutral position where neither procedure occurs, it is easier for the catheter valves to be designed so that they do not allow any suction or oxygen passage access to the atmosphere, during a respective suction or insufflation procedure. While it may be that the oxygen line is pressure relieved through an oxygen relief port during a suction procedure, there is no possibility of any airborne pathogens to escape to the atmosphere during either insufflation or suction procedures. Thus, infection control due to airborne pathogens is much greater.

It should also be noted that, because there is a three position switch so that a neutral position is permitted, whereby the catheter is neither in an insufflation or a suction procedure, it is possible to permit intermittent suction technique while the catheter is being withdrawn from the patient. This is particularly important so as to prevent or preclude damage to very sensitive mucous membranes—which may be particularly severe in newborn infants. The neutral position switch also allows for the catheter to be used in a closed system, as well as in a stand-alone mode.

Moreover, because there is a neutral position, any suctioning or oxygen insufflation procedures may immediately be turned off in the event of an emergency occurring in the patient. By being able to turn off one of such oxygen insufflation or suction procedures without turning on the other, the health care professionals may be more at ease because they know that by setting the catheter valve to its neutral position there is less risk to the patient.

It should also be noted that, because of the simplicity of design and manufacture—which may be totally automated—the dual purpose catheter valve body and the catheter connected to it are completely disposable. In some prior art devices, the valves are, re-used with disposable catheters, so as to reduce the costs of the procedure. However, by doing so, the risk of infection is greatly increased, not only to the patient but to the health care professionals who must handle the valve in its re-use circumstance. Indeed, it is contemplated that dual purpose catheter valves according to the present invention may be supplied and available to the market in the same price range as the previously used thumb control valves discussed above, and at anywhere up to ten times less expensively than certain of the patented prior art devices noted above. By using medical grade material such as polyethylene or particularly polypropylene which may be sterilized using gamma radiation, and automated procedures, not only may the costs of the catheter valve be reduced but also sufficient quantities of the devices may be provided to the market that virtually unlimited numbers of suction/insufflation procedures may be performed.

It is clear that other embodiments, or alterations and amendments to the embodiments of the dual purpose valve taught by the present invention may be made, without departing from the spirit and scope of the appended claims.

I claim:

1. A single-use, disposable input and extraction catheter valve for the respective input or extraction of fluid into or out of a body cavity, comprising:

a valve housing including a first housing piece having an outer cylindrical wall through which, in spaced relationship therearound, there are at least a fluid input port, an extraction port and a catheter port; and a second housing piece having an inner cylindrical wall in fluid tight relationship and concentric with said outer cylindrical wall; said first and second housing pieces forming said valve housing so as to have a generally hollow interior and being rotatable with respect to each other about the axis of the inner and outer cylindrical walls;

wherein said inner cylindrical wall has a first pair of ports therethrough, and a first shut-off portion of its cylindrical wall, whereby said catheter port and said fluid input port are in fluid communication with the interior of the housing, and said extraction port is covered and shut off, when said first and second housing pieces are in a first rotated position, relative to each other;

and wherein said inner cylindrical wall further has a second pair of ports therethrough, with the second pair of ports comprising ports that are different from the first pair of ports, and a second shut-off portion of its cylindrical wall, whereby said catheter port and said extraction port are in fluid communication with the interior of the housing, and said fluid intake port is covered and shut off, when said first and second housing pieces are in a second rotated position, relative to each other;

said inner cylindrical wall further having a third shut-off portion to shut off said catheter port when said first and second housing pieces are in a third rotated position, relative to each other, which is intermediate said first and second positions;

and manually operable means to rotate said first and second housing pieces relative to one another between said first, second and third positions;

wherein said first and second housing pieces can be moved from said first rotated position relative to each other to said second rotated portion relative to each other by being moved substantially less than 90°, wherein said manually operable means is moved only a short distance to obtain said movement of substantially less than 90°; and wherein said catheter valve can be held in one hand, with the thumb of that hand causing said short distance movement between said first and second rotated positions.

2. The input and extraction catheter valve of claim 1, further including an upstanding centrally located hollow post located in said first housing piece, and a centrally located boss on the lower surface of the top of said second housing piece, said hollow post locating said boss therewithin.

3. The input and extraction catheter valve of claim 1, wherein sealing means are provided between the inner surface of said outer cylindrical wall and the outer surface of said inner cylindrical wall, said sealing means comprising a continuous bead on one of said walls located in a complementary groove on the other of said walls.

4. The input and extraction catheter valve of claim 1, wherein a ridge is located in said first housing piece, and the lower inner surface of the cylindrical wall of said second housing piece is tapered downwardly and outwardly, and said ridge is wedge shaped, so that contact of the wedge of said ridge against the tapered lower surface of the second housing piece creates a fluid seal between the pieces.

5. The input and extraction catheter valve of claim 4, where said tapered face of said second housing piece is substantially linear as to its taper, and where the outer surface of said ridge is curved outwardly, whereby the seal is formed having lesser static friction between the wedge and the tapered face.

6. The input and extraction catheter valve of claim 1, where each of said fluid input port, said extraction port, and said catheter port, are substantially circular; and where the two ports of said inner housing piece that are in communication with said catheter port when said housing pieces are in either of said first or second rotated positions, are substantially circular; and wherein the other of said ports of said inner housing piece are elongated so as to be wider around the cylindrical wall than their respective heights.

7. The input and extraction catheter valve of claim 1, further comprising an oxygen relief port formed in the wall of said second housing piece so that it is in fluid communication with said oxygen port when said first and second housing pieces are in said second rotated position, whereby oxygen is vented away from said input and extraction catheter valve through said oxygen relief port.

8. The input and extraction catheter valve of claim 1, where stop means are formed so that when said first and second housing pieces are rotated to any of their first, second or third rotated positions, there is a snap fitting of a complementary means on the other of said pieces to that which has the stop means, and said pieces may be easily engagable and disengagable from each of said stops and snap fitting arrangements.

9. The input and extraction catheter valve of claim 1, wherein the angular movement of said first and second housing pieces from said first rotated position relative to each other to said second rotated position relative to each other is in the order of about 50°.

* * * * *